United States Patent [19]

Trombley, III et al.

[11] Patent Number: 5,591,143
[45] Date of Patent: Jan. 7, 1997

[54] LUER CONNECTOR WITH TORQUE INDICATOR

[75] Inventors: Frederick W. Trombley, III, Gibsonia; Salvatore J. Dedola, McKees Rocks, both of Pa.

[73] Assignee: Medrad Inc., Pittsburgh, Pa.

[21] Appl. No.: 43,911

[22] Filed: Apr. 2, 1993

[51] Int. Cl.$^6$ .................................................. A61M 25/00
[52] U.S. Cl. ........................ 604/283; 604/284; 604/905
[58] Field of Search ............................... 604/283, 32, 34, 604/100, 118, 207–208, 236, 240–243, 178, 284, 165, 166, 167, 158, 256, 186, 189, 169, 210–211, 260, 220, 905; 222/39

[56] References Cited

U.S. PATENT DOCUMENTS

| | | | |
|---|---|---|---|
| 2,564,804 | 8/1951 | Everett | 285/38 |
| 4,198,973 | 4/1980 | Millet | 604/165 |
| 4,294,250 | 10/1981 | Dennehey | 604/403 |
| 4,439,188 | 3/1984 | Dennehey et al. | 604/283 |
| 5,066,286 | 11/1991 | Ryan | 604/240 |
| 5,209,740 | 5/1993 | Bryant et al. | 604/243 |
| 5,330,450 | 7/1994 | Lopez | 604/283 |

*Primary Examiner*—Randall L. Green
*Assistant Examiner*—V. Alexander
*Attorney, Agent, or Firm*—Keck, Mahin & Cate

[57] ABSTRACT

A luer connector is provided with a tactile and audible torque indicator. The indicator comprises a detent incorporated between the female cylindrical component of the luer connector and a rotatable collar mounted thereon. As the collar is turned in a clockwise direction, the collar is impeded by the detent formed by opposingly projecting protuberances between the inside of the collar and the outside of the female cylindrical luer component. As the threaded luer connection is tightened, requiring additional torque to tighten it further, the additional torque overcomes the resistance of the detent, allowing the collar protuberance to slip past the cylinder protuberance. The female luer component may also be provided with a color patch or pattern, to indicate by its rotation, when the detent has been overcome, that the luer connection has been appropriately tightened. In an alternative embodiment, oppositely disposed grooved wings are provided on the rotatable threaded collar of the male luer component to provide indication of proper torque by deflection and failure of the wings just prior to overtightening. The wings may be provided with gussets to strengthen the wings for rotation in the loosening direction.

16 Claims, 2 Drawing Sheets

LUER CONNECTOR WITH TORQUE INDICATOR

BACKGROUND OF THE INVENTION

This invention relates generally to connectors and the like and relates more particularly to improvements in luer connectors. Luer connectors are commonly used in the field of clinical medicine to mate and connect corresponding ends of fluid conduits. Such conduits may include tubing, syringes and other such apparatus.

A luer connector includes two matable components: (1) a male tip with a rotatable collar having internal threads, and (2) a female receptacle to receive the male tip and having corresponding external threads. When the corresponding threads are screwed together, the male tip and the female receptacle are drawn together to form a tight fit. A problem which may develop in such connectors arises because the connectors are typically made of plastic material, such as polycarbonate, to allow for economical manufacture and disposability. Luer connectors are typically designed to be fully connective after a 90- or 180-degree turn. To establish the proper fit, the correct relative torque should be applied between the two interconnecting components. If too little torque is applied, the connection may fail to be fluid tight. If too much torque is applied to the connector pair, on the other hand, the connector's threads may be stripped, causing the connection to fail.

In order to provide a luer connector which overcomes the problem of undertightening or overtightening, it is necessary to provide a ready indication that the proper relative torque has been applied. The present invention solves this problem by providing audible, tactile and visible indications when such appropriate torque has been applied. The use of this invention is intended to provide a connection that will promote the highest degree of user confidence regarding proper attachment.

SUMMARY OF THE INVENTION

It is an object of the present invention to provide a luer connector which includes a torque indicator to alert a user that proper torque has been applied to and between interconnecting luer components to fully connect them.

It is a further object of the present invention to provide a luer connector which includes an audible indicator of proper torque.

It is a further object of the present invention to provide a luer connector which includes a tactile indicator of proper torque.

It is a further object of the present invention to provide a luer connector which includes a visible indicator of proper torque to indicate proper connection of the luer fitting to observers not involved in the connection process.

Another object of the invention is to provide a luer connector which includes wing members to provide turning leverage, but which are designed to fail at a predetermined appropriate torque.

The invention in a specific and preferred embodiment relates to a luer connector with a torque indicator. The luer connector of the present invention comprises a male luer component which has a tapered male luer tip surrounded by a rotatable, internally threaded collar. The corresponding female luer component includes a cylinder having an axial socket to accommodate the male luer tip with external threads corresponding to the internal threads on the collar of the male component.

In the preferred embodiment of the present invention, the female luer component also includes a rotatable collar which is freely rotatable through a limited range around the female cylinder. The rotatable collar has an inwardly facing ridge which abuts an outward radiating land portion from the female cylinder to limit the range of rotation of the collar. At an intermediate point of the range of rotation of the collar, the female cylinder is provided with an outwardly projecting knob lower in height than the land, to provide resistance to the internal ridge of the rotatable collar. To connect the two luer components, the rotatable collar is turned against the knob in a tightening direction until reaching the appropriate pre-determined torque. At that point, the applied torque necessary to fully tighten the luer connector overcomes the resistance of the knob against the ridge, and the ridge slips past the knob, providing a tactile and audible indication that the torque has been reached.

The rotatable collar and the female cylinder of the female luer component may be color coded so that, when the rotatable collar slips past the resistance of the knob and abuts the end of its rotational freedom, the position of the color coding will indicate that the connection is fully seated.

A second embodiment of the luer connector provides a different means of torque-induced failure. In this embodiment, the rotatable collar of the male luer component is provided with wings which provide leverage when the male component is gripped between thumb and forefinger to enable the user to tighten the luer lock like a wing nut. In this embodiment, the wings are axially and radially aligned, and provided with longitudinal grooves parallel and adjacent to the collar, allowing the wings to fail in the direction away from the grooves when sufficient torque has been applied to the luer lock to properly complete the connection. The wings may be provided with gussets on the same side as the grooves to provide additional structural rigidity for application of torque to disconnect the luer lock.

DESCRIPTION OF THE DRAWING FIGURES

DESCRIPTION OF THE PREFERRED EMBODIMENT

Figure 1:
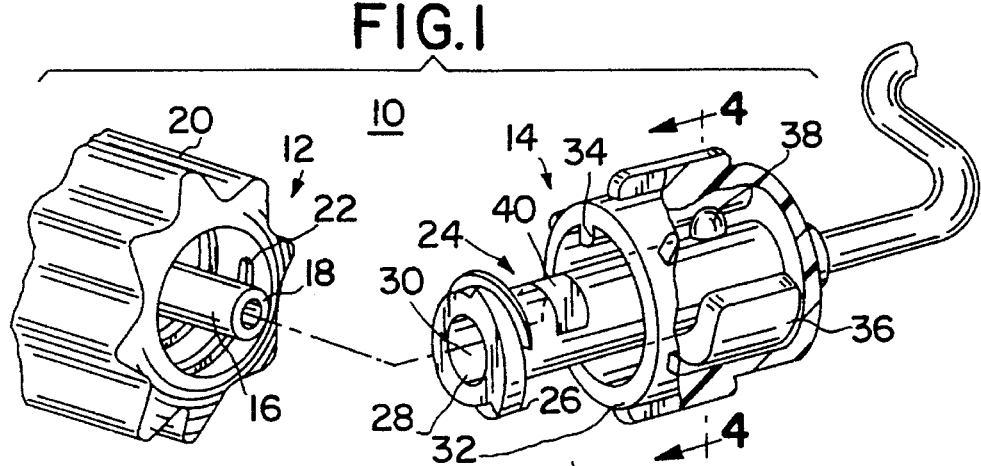
FIG. 1 is a general perspective view of a luer lock embodying the present invention, wherein the collar of the female luer component is shown partially cut away.

Referring now to the drawings, and particularly to FIG. 1 thereof, there is shown one embodiment of a luer connector according to the present invention 10, which includes male luer component 12 and female luer component 14. Male luer component 12 includes generally tubular tip 16 which is tapered toward open end 18. Male tip 16 and rotatable knurled collar 20 are coaxial. Collar 20 has internal threads 22. Female luer component 14 includes female cylinder 24. Female cylinder 24 has external threads 26 adjacent opening 28. Opening 28 leads to tapered tubular receptacle 30, which corresponds in size and shape to, and is matable with, tapered tubular tip 16. Also provided is collar 32 which is rotatably mounted to female cylinder 24. Collar 32 has inwardly disposed ridge 34. Female cylinder 24 has land 36 and knob 38 projecting from the surface of female cylinder 24 and located on opposite sides thereof. Land 36 projects farther from the surface of cylinder 24 than knob 38. Also provided on cylinder 24 is color indicator patch 40. Color indicator patch 40 may be a single color or a color pattern to appear as a visible torque indication, as will be more fully described below.

Figure 2:
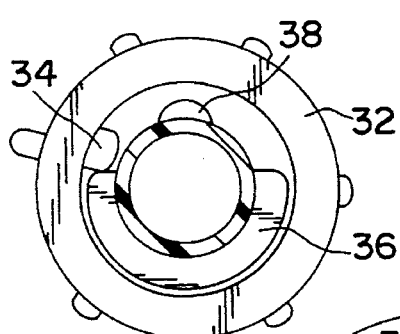
FIG. 2 is a view of the female luer component taken at Line 4—4 of FIG. 1, but showing the component at a prior stage of rotation.
Figure 3:
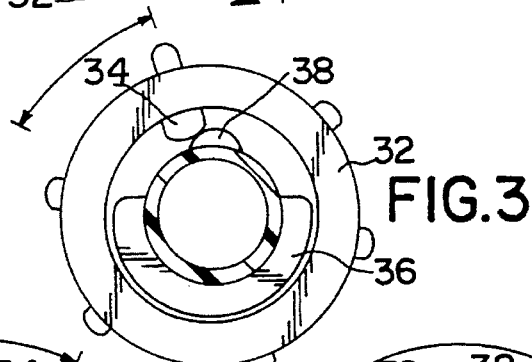
FIG. 3 is a view of the female luer component taken along Line 4—4 of FIG. 1, but showing the rotatable collar in position to turn the female luer component.
Figure 4:
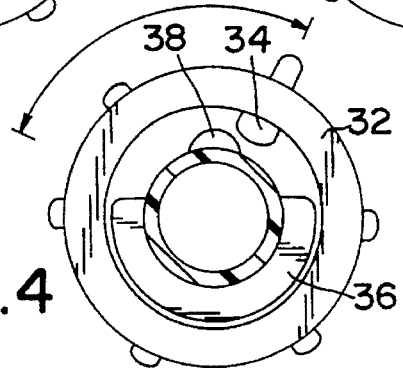
FIG. 4 is a view of the female luer component taken along Line 4—4 of FIG. 1, wherein the rotatable collar has slipped past the knob of the female luer component.
Figure 5:
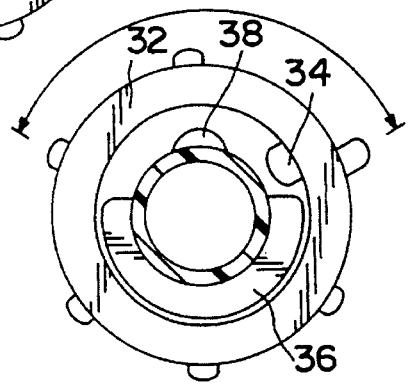
FIG. 5 is a view of the female luer component taken along Line 4—4 of FIG. 1, wherein the rotatable collar is shown at the end of its rotational travel.
Figure 6:
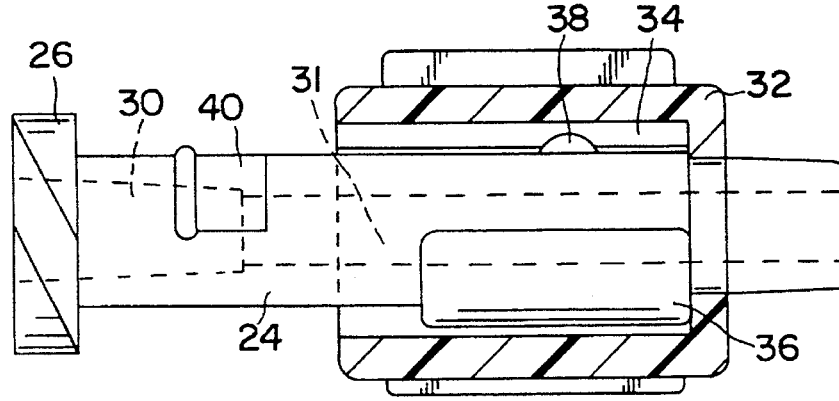
FIG. 6 is a side view of the female luer component shown in Section 1, partially cut away.

A different view of female luer component 14 is presented at FIG. 6. FIGS. 2–5 illustrate the operation of the luer lock embodying the present invention as clockwise torque is applied to rotatable collar 32 to attach a female luer component 14 to male luer component 12. Initially, knob 34 is located at the 10 o'clock position, abutting land 36 as shown in FIG. 2. As collar 32 is turned in a clockwise direction, it approaches the 11 o'clock position shown in FIG. 3, where its clockwise progress is impeded by knob 38. The sum of the inward radial dimension of ridge 34 and the outward radial dimension of knob 38 is only slightly greater than the distance between the outer surface of cylinder 24 and the inner surface of collar 32. As collar 32 is turned clockwise, it urges knob 38 and cylinder 24 in a clockwise rotation. This rotation tightens female external threads 26 onto internal threads 22 of male collar 20, drawing the male tip and the female receptacle together.

As the male and female luer components are drawn together, the resistance to further tightening increases. At a pre-determined torque value, corresponding to the proper seating of the connector, the resistance offered is greater than the relative resistance presented between ridge 34 and knob 38. Further tightening of the connector applies greater torque to collar 32. This additional torque overcomes the resistance between ridge 34 and knob 38 so that ridge 34 slips over and past knob 38 to the 1 o'clock position shown in FIG. 4. The effort required to turn collar 32 lessens appreciably after that point, and collar 32 is freely rotatable through the remainder of its travel to the 2 o'clock position abutting land 36 as shown in FIG. 5.

While the elements 34, 38 and 36 of female luer component 14 have been shown and described herein as a ridge, a knob and a land, respectively, it should be readily understood that the same operations can be accomplished by different configurations of these protuberances. For example, elements 34 and 38 could be configured as aligned knobs or bumps, and land 36 could be configured as oppositely radially extending ridges, to axially retain collar 32 and to act as abutments to limit the rotational range of collar 32.

In the operation of the luer connector as described above, when ridge 34 slips past knob 38, the user is presented with a distinct tactile sensation of overcoming this detent. This overcoming of resistance also emits a "click" as the resistance is overcome. In this manner, the achievement of appropriate torque to tighten the luer connector provides a tactile and audible indication of predetermined torque, and therefore, proper connection.

Color patch 40 on cylinder 24 is rotated to a new position by the travel of rotatable collar 32 past the detent to its final location through its free rotation. In this manner, the change in position of color patch 40 is displayed in a different alignment and provides a visual indication that proper torque has been applied and that the luer connector is properly mated. Thus, the fully connected nature of the apparatus is readily apparent to any other viewer.

The luer connector of the present embodiment has been shown and described to include a torque indicator mounted on the female component of the luer connector. It will be readily appreciated, however, that the torque indicator of the present invention, either in the form described above or in alternate embodiments, such as that to be described below, may be operably mounted on either the male or female components of the luer connector. The choice of placement of the torque indicator will be dictated by the circumstances of the particular use. For example, a syringe/tubing connection may include a male luer component formed at the end of a syringe, to be mated to a female luer component attached to a length of tubing. The configuration will typically require the association of the torque indicator on the female component. Other configurations and connection types may benefit from incorporating the torque indicator on the male luer component, as in the following alternative embodiment.

DESCRIPTION OF AN ALTERNATIVE EMBODIMENT

Figure 7:
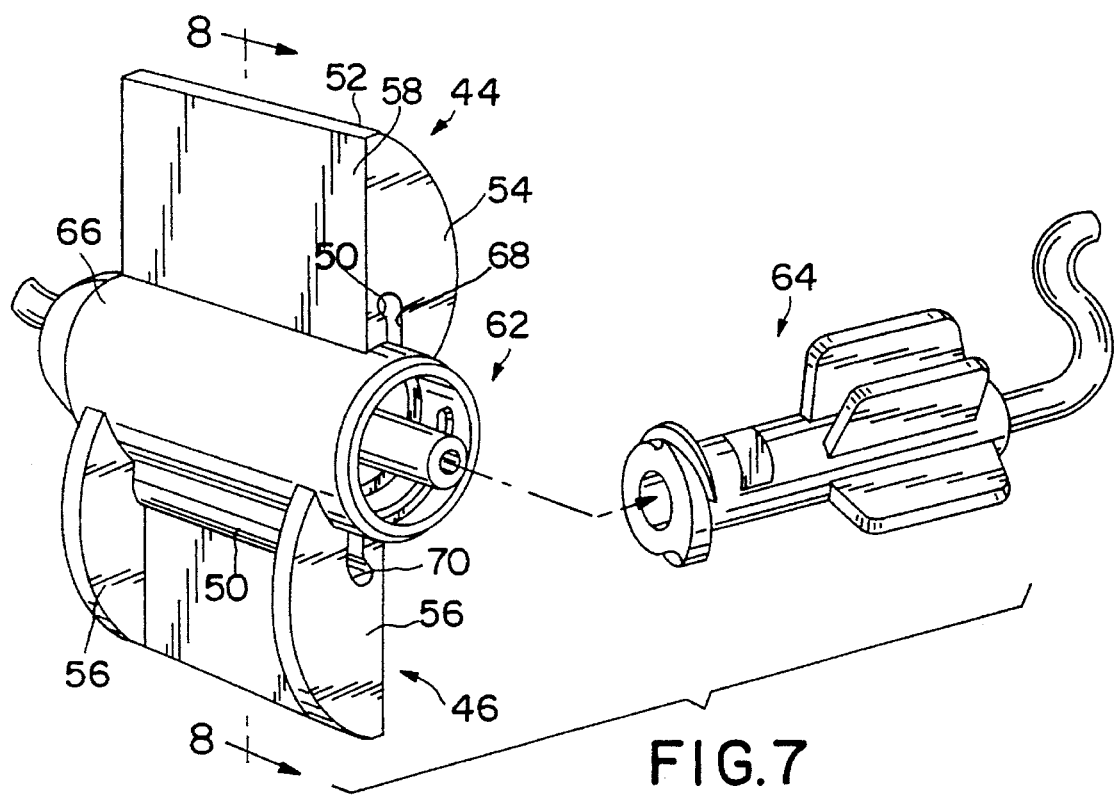
FIG. 7 is a general perspective view of a second embodiment of the present invention, showing the mating portions of the luer connector.
Figure 8:
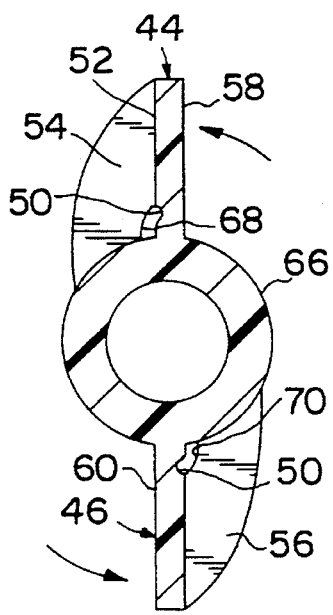
FIG. 8 is a view of the male luer connector collar taken along Line 8—8 of FIG. 7.
Figure 9:
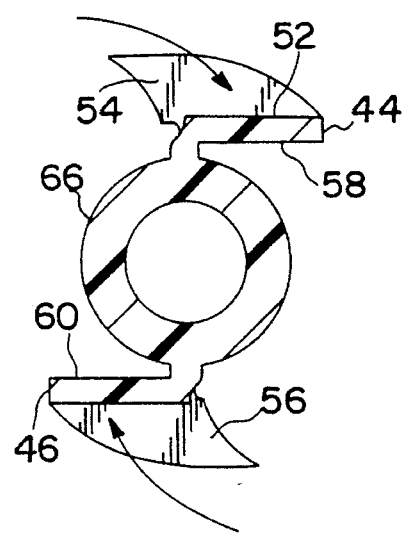
FIG. 9 is another view of the male luer connector collar as shown at FIG. 8, showing the failure of the wings of the female luer component at pre-determined torque.

An alternative embodiment of the present invention is shown at FIGS. 7–9. In this embodiment, male luer component 62 is matable with female luer component 64, as shown in FIG. 7. Oppositely disposed wings 44 and 46 on rotatable collar 66 are axially aligned with collar 66 and project radially therefrom. As shown in these figures, wing 44, and oppositely disposed wing 46 include axially defined grooves 50, which are cut into wings 44 and 46 and extend throughout the entire length of wings 44 and 46.

Groove 50 in wing 44 is parallel to the axis of cylinder 48 of male component 62 and adjacent to the surface of rotatable collar 66. Groove 50 serves to weaken the structure of wing 44 so that when significant pressure is applied to inside face 52 of wing 44, wing 44 may be deformed backwards at groove 50 as shown in FIG. 9. When the pressure is released from wing 44, the resilient plastic material of wing 44 regains its original upright orientation.

Also provided on wings 44 and 46 are gusset pairs 54 and 56 respectively. In the case of wing 44, gusset pair 54, abutting the surface of cylinder 48, provides structural rigidity to wing 44 when pressure is applied to wing 44 on outside face 58, to turn male component 62 in a direction to disconnect the luer components. Gusset pairs 54 and 56 have undercuts 68 and 70, respectively. Gusset pairs 54 and 56 are attached to wings 44 and 46 above grooves 50.

In operation, wings 44 and 46 may be gripped by the user's thumb and forefinger to apply pressure against the inner faces of wings 44 and 46 to turn collar 66 in a tightening direction to screw collar 66 onto the threads of female component 64. When the increased resistance offered by the seating of male tip 16 within female receptacle 30 reaches a predetermined value, the wings 44 and 46 will deflect and collapse because the resistance offered by the threads is greater than the resistance offered by the structurally weakened grooved wings.

In this way the winged configuration of this embodiment effectively limits the relative torque which can be applied to the luer connector pair. Thus, the failure of wings 44 and 46 provides an additional safeguard to the luer connect beyond merely indicating that sufficient torque has been applied.

When the resilient wings are released, they will tend to revert to their original upright posture. To disconnect the luer connection, the wings are grasped and pressure is applied in opposite directions to the outer faces 58 and 60, respectively, of wings 44 and 46. Gussets 54 and 56 provide wings 44 and 46, respectively, with much greater structural strength in the loosening direction, allowing for ready disconnection without significant deflection or failure of wings 44 and 46.

The wings in this alternative embodiment of the present invention may be designed to permanently fail when the proper relative torque has been applied by the user to the luer connector. These deformed or bent wings or tabs would provide a permanent visual indication of proper connection.

While the invention has been described in connection with preferred embodiments, it will be understood that it is not intended to limit the invention thereto, but is intended to cover all modifications and alternative constructions falling within the spirit and scope of the invention as expressed in the appended claims.

We claim:

1. A luer connector comprising:

a threaded male luer component;

a threaded female luer component rotationally engageable with said male luer component; and a first protuberance comprising indication means connected to at least one of said luer components for tactilely indicating, after the male and female luer components have been connected, that a predetermined torque has been applied to said connector to complete a fluid-tight seal between the male and female luer components and to warn against overtightening of said connector; and a second protuberance comprising deflectable means connected to at least one of said luer components for preventing further application of torque after said predetermined torque has been applied, wherein said first protuberance and said second protuberance cooperate together to provide a tactile response.

2. A luer connector as in claim 1, further comprising means for visually indicating that the predetermined torque has been applied to said connector to complete the fluid-tight seal.

3. A luer connector as in claim 1, wherein said indication means comprises at least one deflectable wing member attached to and radiating from one of said luer components, wherein said wing member is deflected by the application of a predetermined torque to said wing to fully tighten said luer connector.

4. A luer connector as in claim 3, wherein said wing member is substantially permanently deformable by failure of said wing member upon application of predetermined torque, to provide a visual indication of proper luer connection.

5. A luer connector comprising:

a threaded male luer component;

a threaded female luer component rotationally engageable with said male luer component; and indication means connected to at least one of said luer components for tactilely indicating, after the male and female luer components have been connected, that a predetermined torque has been applied to said connector to complete a fluid-tight seal between the male and female luer components and to warn against overtightening of said connector; and deflectable means connected to at least one of said luer components for preventing further application of torque after said predetermined torque has been applied, wherein said tactile indication means comprises a collar rotatably mounted on one of said luer components; and detent means connected to one of said luer components to retard the rotation of said collar on said component to allow tightening of the luer components together until sufficient resistance is encountered to require torque sufficient to overcome the resistance of said detent means.

6. A luer connector as in claim 5, wherein said detent means comprises an inwardly projecting first protrusion formed on said collar, and an outwardly projecting second protrusion formed on said luer component contacting said first protrusion upon relative rotation of said collar around said component;

thereby offering resistance to the rotation of said collar around said component only until said predetermined torque is applied to said collar to overcome said resistance.

7. A luer connector comprising:

a threaded male luer component;

a threaded female luer component rotationally engageable with said male luer component; and indication means connected to at least one of said luer components for tactilely indicating, after the male and female luer components have been connected, that a predetermined torque has been applied to said connector to complete a fluid-tight seal between the male and female luer components and to warn against overtightening of said connector; and means for visually indicating that the predetermined torque has been applied to said connector to complete the fluid-tight seal; and deflectable means connected to at least one of said luer components for preventing further application of torque after said predetermined torque has been applied;

therein said visual indication means comprises a color patch applied to at least one of said male and female components, whereby the rotational position of said color patch provides an indication that sufficient relative torque has been applied to said connector to complete the fluid-tight seal.

8. In a luer connector having a threaded male luer component and a threaded female luer component rotationally engageable with said male luer component, the improvement comprising a first protuberance which comprises indication means connected to at least one of said luer components for tactilely indicating, after the male and female luer components have been connected, that a predetermined torque has been applied to said connector to complete a fluid-tight seal between the male and female luer components and to warn against overtightening of said connector; and a second protuberance which comprises deflectable means connected to at least one of said luer components for preventing further application of torque after said predetermined torque has been applied, wherein said first protuberance and said second protuberance cooperate together to provide a tactile response.

9. A luer connector comprising:

a threaded male luer component;

a threaded female luer component rotationally engageable with said male luer component; and indication means connected to at least one of said luer components for tactilely indicating, after the male and female luer components have been connected, that a predetermined torque has been applied to said connector to complete a fluid-tight connector seal between the male and female luer components and to warn against overtightening of said connector; and deflectable means connected to at least one of said luer components for preventing further application of torque after said predetermined torque has been applied;

wherein said indication means comprises a collar rotatably mounted on one of said luer components; and detent means connected to one of said luer components for retarding the rotation of said collar, said detent means prohibiting tightening of the luer connector after a predetermined torque sufficient to overcome the resistance of said detent means is applied.

10. A luer connector as in claim 9, wherein said detent means comprises an inwardly projecting first protrusion formed on said collar; and an outwardly projecting second protrusion formed on said luer component intermittently contacting said first protrusion;

thereby offering resistance to the rotation of said collar around said component until a predetermined torque is applied to said collar to overcome said resistance.

11. A luer connector comprising:

a threaded male luer component;

a threaded female luer component rotationally engageable with said male luer component; and indication means connected to at least one of said luer components for tactilely indicating, after the male and female luer components have been connected, that a predetermined torque has been applied to said connector to complete a fluid-tight connector seal between the male and female luer components and to warn against overtightening of said connector; and wherein said indication means are deflectable and are connected to at least one of said luer components for preventing further application of torque after said predetermined torque has been applied;

wherein said indication means comprises at least one deflectable wing member attached to and radiating from one of said luer components;.

wherein said wing member is deflected by the application of a predetermined torque to said wing to fully tighten said luer connector; and wherein said wing member includes a longitudinal groove defined in said wing member adjacent to and axially parallel to said one of said luer components to structurally weaken said wing member to allow said wing member to fail upon application of said predetermined torque.

12. A luer connector as in claim 11, wherein said wing member has a first side and a second side and includes at least one gusset member attached to said first side and abuttable with said one of said luer components so that said gusset member will brace said wing against force applied to said second side, thereby preventing failure of said wing member.

13. A luer connector comprising:

a threaded male luer component;

a threaded female luer component rotationally engageable with said male luer component; and a first protuberance comprising tactile indication means cooperating with the male luer component and the female luer component to provide tactile indication, after the male and female luer components have been connected, of a predetermined torque being reached upon relative rotation of said male and female components, said predetermined torque being that just necessary to effect a fluid-tight seal between the male and female luer components and to warn against overtightening of said connector; and a second protuberance comprising deflectable means connected to at least one of said luer components for preventing further application of torque after said predetermined torque has been applied, wherein said first protuberance and said second protuberance cooperate together to provide a tactile response.

14. A luer connector comprising:

a threaded male luer component;

a threaded female luer component rotationally engageable with said male luer component; and a first protuberance comprising audible indication means cooperating with the male luer component and the female luer component to provide audible indication, after the male and female luer components have been connected, of a predetermined torque being reached upon relative rotation of said male and female components, said predetermined torque being that just necessary to effect a fluid-tight seal between the male and female luer components and to warn against overtightening of said connector; and a second protuberance comprising deflectable means connected to at least one of said luer components for preventing further application of torque after said predetermined torque has been applied, wherein said first protuberance and said second protuberance cooperate together to provide a tactile response.

15. A luer connector as in claim 14, further comprising means for visually indicating that the predetermined torque has been applied to said connector to complete the fluid-tight seal.

16. A luer connector comprising:

a threaded male luer component;

a threaded female luer component rotationally engageable with said male luer component; and audible indication means cooperating with the male luer component and the female luer component to provide audible indication, after the male and female luer components have been connected, of a predetermined torque being reached upon relative rotation of said male and female components, said predetermined torque being that just necessary to effect a fluid-tight seal;

deflectable means connected to at least one of said luer components for preventing further application of torque after said predetermined torque has been applied;

means for visually indicating that the predetermined torque has been applied to said connector to complete a fluid-tight connection;

wherein said visual indication means comprises a color patch applied to at least one of said male and female luer components, whereby the rotational position of said color patch provides an indication that sufficient relative torque has been applied to said connector to complete the fluid-tight seal.

* * * * *